United States Patent [19]

Sturm et al.

[11] 4,333,949
[45] Jun. 8, 1982

[54] 1H-INDEN-1-ONE DERIVATIVES, THEIR USE IN MICROBICIDAL COMPOSITIONS, AND FOR COMBATING MICROORGANISMS

[75] Inventors: Elmar Sturm, Aesch; Robert Nyfeler, Basel, both of Switzerland

[73] Assignee: Ciba-Geigy Corporation, Ardsley, N.Y.

[21] Appl. No.: 270,714

[22] Filed: Jun. 5, 1981

Related U.S. Application Data

[62] Division of Ser. No. 89,830, Oct. 31, 1979, Pat. No. 4,291,061.

[30] Foreign Application Priority Data

Nov. 6, 1978 [CH] Switzerland ............... 11528/78

[51] Int. Cl.³ ............... A01N 47/10; C07C 125/04, C07C 125/067
[52] U.S. Cl. ............... 424/300; 424/331; 560/22; 560/29; 560/31; 560/32; 560/134; 560/139; 560/33; 560/65; 560/73; 560/115; 260/465 D; 568/306; 568/315; 568/327
[58] Field of Search ............... 560/134, 560/22, 20, 29, 31, 32, 115, 33; 260/465 D; 424/300

[56] References Cited

U.S. PATENT DOCUMENTS

| | | | |
|---|---|---|---|
| 2,870,057 | 1/1959 | Hartle et al. | 560/134 |
| 3,084,906 | 4/1963 | Lambrech | 560/134 |
| 3,597,472 | 8/1971 | Heiss | 560/134 |
| 3,712,915 | 1/1973 | Seyberlich et al. | 560/134 |
| 4,107,324 | 8/1978 | Grotkopp et al. | 560/134 |
| 4,228,181 | 10/1980 | Grotkopp et al. | 560/134 |

OTHER PUBLICATIONS

Bergmann, J.A.C.S., vol. 81, pp. 5641-5643 (1959).

*Primary Examiner*—Natalie Trousof
*Assistant Examiner*—Frederick W. Pepper
*Attorney, Agent, or Firm*—Frederick H. Rabin

[57] ABSTRACT

2,3-Dichloro-7-hydroxy-1H-inden-1-one derivatives of the formula I

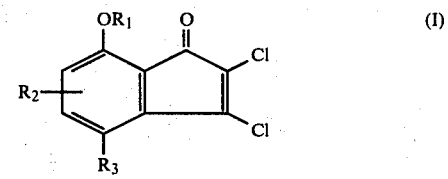

(I)

wherein
$R_1$ is hydrogen or one of the groups

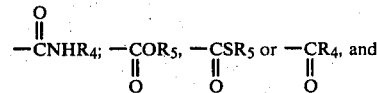

$R_2$ and $R_3$ independently of one another are each hydrogen, fluorine, chlorine, bromine, $C_1$–$C_4$-alkyl, trifluoromethyl or nitro,
$R_4$ is hydrogen, $C_1$–$C_6$-alkyl or $C_2$–$C_4$-alkenyl, each of which is unsubstituted or substituted by halogen, or $R_4$ is phenyl which is unsubstituted or is substituted by $C_1$–$C_4$-alkyl, $C_1$–$C_4$-alkoxy, halogen, trifluoromethyl, cyano or nitro, or it is a $C_3$–$C_6$-cycloalkyl group, and
$R_5$ is $C_1$–$C_6$-alkyl, $C_3$–$C_6$-cycloalkyl or $C_2$–$C_4$-alkenyl.

These compounds exhibit a microbicidal action against in particular phytopathogenic fungi and bacteria.

13 Claims, No Drawings

1H-INDEN-1-ONE DERIVATIVES, THEIR USE IN MICROBICIDAL COMPOSITIONS, AND FOR COMBATING MICROORGANISMS

This is a division of application Ser. No. 089,830 filed on Oct. 31, 1979 now U.S. Pat. No. 4,291,061.

The present invention relates to 2,3-dichloro-7-hydroxy-1H-inden-1-one derivatives of the formula

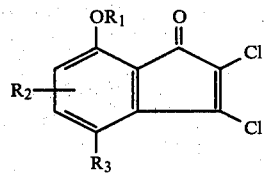

wherein
$R_1$ is hydrogen or one of the groups

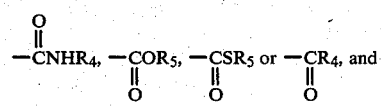

$R_2$ and $R_3$ independently of one another are each hydrogen, fluorine, chlorine, bromine, $C_1$–$C_4$-alkyl, trifluoromethyl or nitro, $R_4$ is hydrogen, $C_1$–$C_6$-alkyl or $C_2$–$C_4$-alkenyl, each of which is unsubstituted or substituted by halogen, or $R_4$ is phenyl which is unsubstituted or is substituted by $C_1$–$C_4$-alkyl, $C_1$–$C_4$-alkoxy, halogen, trifluoromethyl, cyano or nitro, or it is a $C_3$–$C_6$-cycloalkyl group, and $R_5$ is $C_1$–$C_6$-alkyl, $C_3$–$C_6$-cycloalkyl or $C_2$–$C_4$-alkenyl.

As alkyl or as alkyl part of another substituent are meant, depending on the given number of C atoms, the following groups: methyl, ethyl, propyl, butyl, pentyl and hexyl, and also isomers thereof, such as iso-propyl, iso-butyl, sec-butyl, tert-butyl and iso-pentyl.

Halogen is fluorine, chlorine, bromine or iodine.

Alkenyl is for example: allyl, 2-butenyl or methallyl, as well as groups substituted by halogen, such as chloroallyl or trichlorovinyl. $C_3$–$C_6$-cycloalkyl embraces cyclopropyl, cyclobutyl, cyclopentyl and cyclohexyl.

The compounds of the formula I are highly effective microbicides.

The compounds of the invention can be produced by
(a) reacting a compound of the formula II

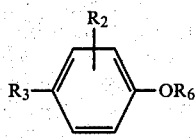

wherein $R_2$ and $R_3$ have the meanings defined under the formula I, and $R_6$ is hydrogen or preferably methyl, with trichloroacrylic acid chloride of the formula

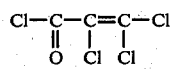

in the presence of a Lewis acid; and (b) reacting the resulting compound of the formula IV

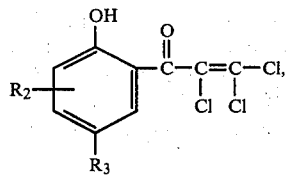

likewise in the presence of a Lewis acid, to give a compound of the formula V

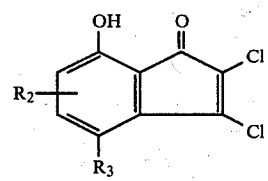

which corresponds to a compound of the formula I wherein $R_1$ is hydrogen; and (c), in order to produce compounds of the formula I wherein $R_1$ has a meaning other than hydrogen, reacting the compound of the formula V with an acid halide, isocyanate, haloformic acid ester or halothioformic acid ester, corresponding in each case to the meaning of $R_1$.

The processes are optionally performed in the presence of solvents inert to the reactants. Suitable solvents for stage (a) are for example: anhydrous halogenated hydrocarbons such as chloroform, methylene chloride, carbon tetrachloride, and also carbon disulfide, etc. Suitable solvents for stage (b) are for example: nonreactive aromatic hydrocarbons, such as trichlorobenzene or nitrobenzene; and stage (b) may also be performed with the reactants forming an anhydrous melt. And suitable solvents for stage (c) are for example: (i) in the case of acid halides and halo(thio)formic acid esters: aliphatic or aromatic hydrocarbons such as benzene, toluene, xylenes or petroleum ether; halogenated hydrocarbons, such as chlorobenzene, methylene chloride, ethylene chloride or chloroform; ethers and ethereal compounds, such as dialkyl ether, dioxane or tetrahydrofuran; nitriles such as acetonitrile; N,N-dialkylated amides, such as dimethylformamide; dimethyl sulfoxide, ketones, such as methyl ethyl ketone; and mixtures of solvents of this type; and acid-binding agents may be added, for example the hydroxides, carbonates, and so forth, of alkali metals and alkaline-earth metals, or nitrogen bases, such as pyridine and trialkylamines; and (ii) in the case of the isocyanates: anhydrous solvents, such as ethers, tetrahydrofuran, dioxane or dimethylformamide, and, as catalyst, trialkylamines.

Suitable Lewis acids are for example customary representatives such as boron trifluoride, titanium tetrachloride, tin tetrachloride, iron(III)chloride (anhydrous) and zinc chloride, particularly however aluminium trichloride.

The reaction temperatures for stage (a) are between 20° and 120° C., for stage (b) between 130° and 180° C., and for stage (c) between 0° and 180° C. The processes are performed under normal pressure.

By using two equivalents of Lewis acid, relative to acid chloride and aromatic hydrocarbons, at the commencement of the reaction, with a temperature of 130°–180° C., it is possible to combine the two stages (a) and (b) into a single-vessel process. In this case too the preferred Lewis acid is AlCl₃.

In a modification of the process described above, it is possible in the case of those compounds of the formula I wherein R₂ in the 6-position is not hydrogen to introduce this substituent advantageously after completion of stage (b) into a compound of the formula Va

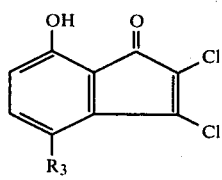

by known methods of aromatic substitution. This applies for nitro and halogen.

With compounds of the formula II wherein R₂ is in the meta-position, the Friedel-Crafts reaction results in a product which is not homogeneous, because the reaction yields, in addition to the actual compound of the formula IV, when R₃=H, two isomeric compounds of the formulae IVa and IVb, and, when R₃≠H, one isomeric compound IVa

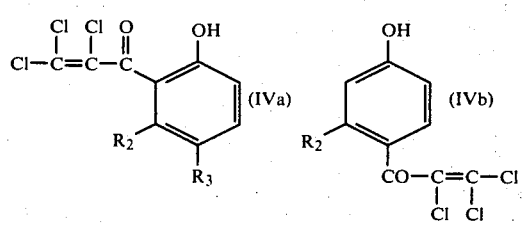

which lead to undesired and/or undefined final products. Their removal from the further course of reaction is effected for example by column chromatography.

In the case of stage (a) of the process described above, defined intermediates of the formula IV can be isolated at temperatures below 100° C. and/or with shorter reaction times (<1 hour).

Only with a higher temperature, longer duration and an excess of Lewis acid (AlCl₃) are there formed the compounds of the formula V by inner-molecular Friedel-Crafts alkenylation in the single-vessel process already mentioned.

The compounds of the formula IV are novel; they likewise form subject matter of the present invention and have a remarkable fungicidal and bactericidal action. They can moreover be used for producing polymers and copolymers and as dye-coupling components.

The said compounds can also be obtained by reaction of a compound of the formula VI

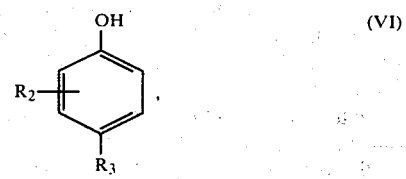

in the presence of a base, with trichloroacrylic acid chloride. There is firstly formed the following compound

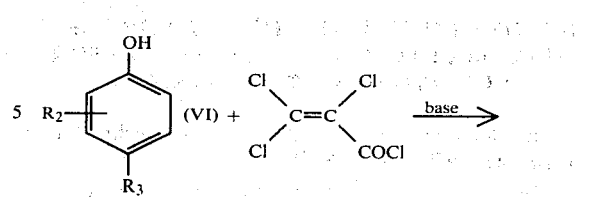

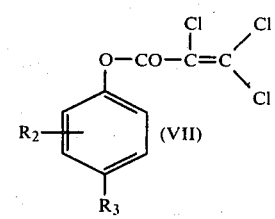

The desired compound IV is obtained by a Fries displacement from VII, in the presence of a Lewis acid (preferably aluminium trichloride), in an inert solvent.

The processes described above likewise form part of the present invention.

The substituted anisoles of the formula II are commercial synthetics, or they can be produced for example from the corresponding phenols by methylation with dimethyl sulfate, trimethyl phosphate, or the like.

The compounds of the formulae I and IV can be used on their own or together with suitable carriers and/or other additives. Suitable carriers and additives can be solid or liquid and they correspond to the substances common in formulation practice, such as natural or regenerated mineral substances, solvents, dispersing agents, wetting agents, adhesives, thickeners, binders or fertilisers. Compositions of this type are produced, in a manner known per se, by intimate mixing and grinding of the constituents. For application, the compounds of the formulae I and IV can be in the following forms (the weight-percentage values in brackets signify advantageous amounts of active substance).

solid preparations: dusts and scattering agents (up to 10%); granulates [coated granules, impregnated granules and homogeneous granules] or pellets (1 to 80%);

liquid preparations:

(a) water-dispersible concentrates of active substance: wettable powders and pastes (25–90% in the commercial packing, 0.01–15% in ready-for-use solutions); emulsions and solution concentrates (10–50%, 0.01–15% in ready-for-use solutions);

(b) solutions and aerosols.

The content of active substance in the above described compositions is between 0.1 and 95 percent by weight. Compositions of this kind are likewise subject matter of the present invention.

In order to adapt them to prevailing circumstances and to broaden their sphere of action, the compounds of the formulae I and IV can of course be used together with other suitable pesticides, for example with fungicides, bactericides, insecticides, acaricides or herbicides, or with active substances influencing plant growth. Such compositions too form part of the subject matter of the present invention.

The compounds of the formulae I and IV exhibit a very favourable microbicidal spectrum for practical requirements for the protection of cultivated plants, without affecting the plants disadvantageously by producing undesirable secondary effects. Cultivated plants within the scope of the present invention are for example: cereals, maize, rice, vegetables, sugar beet, soya bean, groundnuts, fruit trees, ornamental plants, grape vines, hops, Cucurbitaceae (cucumbers, pumpkins and melons), Solanaceae, such as potatoes, tobacco and tomatoes, as well as bananas, cocoa and natural rubber plants.

Fungi occurring on plants or on parts of plants (fruit, blossom, foliage, stalks, tubers or roots) of the said crops and of related cultivated crops can be inhibited or destroyed with the active substances of the formulae I and IV, and also parts of plants subsequently growing remain preserved from such fungi. The active substances are effective against phytopathogenic fungi belonging to the following classes: Ascomycetes (for example Venturia, Helminthosporium and Fusarium); Basidiomycetes, such as in particular rust fungi (for example Puccinia and Tilletia); Fungi imperfecti (for example Botrytis, Piricularia and Cercospora); and against Oomycetes belonging to the Phycomycetes class, such as Plasmopara. The active substances are also effective against phytopathogenic bacteria, for example Pseudomonas spp. and Xanthomonas spp., as well as Erwinia and Corynebacterium. Furthermore, the compounds of the invention have in some cases as systemic action. They can also be used as dressing agents for the treatment of seed (fruit, tubers and grain), and of plant cuttings to protect them against infections, and also against phytopathogenic microbes occurring in the soil. The present invention relates therefore also to the use of compounds of the formulae I and IV for combating microorganisms.

The following types of substituents and also combinations of these among each other constitute preferred embodiments of the invention:

$R_1$ is hydrogen or

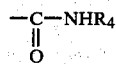

$R_2$ in the 6-position is hydrogen, nitro or halogen, and $R_4$ is methyl or ethyl.

Of interest are also compounds of the formula I wherein $R_1$ is hydrogen,

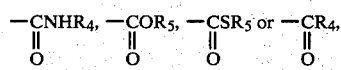

$R_2$ is hydrogen or (in the 6-position) nitro, fluorine, chlorine or bromine, or (in the 5-position) fluorine, chlorine or bromine, $R_3$ is hydrogen, fluorine, chlorine or bromine or $C_1$-$C_4$-alkyl, $R_4$ is $C_1$-$C_4$-alkyl or $C_2$-$C_3$-alkenyl each unsubstituted or substituted by halogen, and $R_5$ is $C_1$-$C_4$-alkyl.

The Examples which follow serve to further illustrate the invention without limiting the scope thereof. The temperature values are given in degrees Centigrade, pressure values are in millibars, and 'parts' and percentage values relate to weight.

Production Examples

Example 1 (single-vessel process)

Production of 2,3-dichloro-7-hydroxy-4-methyl-1H-inden-1-one of the formula

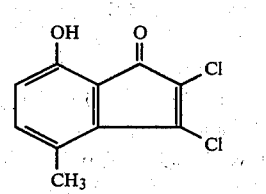

122 g of p-cresol-methyl ether and 194 g of trichloroacrylic acid chloride were dissolved in 500 ml of 1,2,4-trichlorobenzene. To the stirred mixture was added 330 g of anhydrous aluminium chloride in portions, in the course of which the temperature rose to about 50°. The temperature was then raised to 80°, with a uniform stream of hydrogen chloride being released. The temperature was finally raised to 120°, and the mixture was stirred for a further 4 hours. After cooling, the dark-brown reaction mixture was introduced into ice-water, whereupon 140 g of yellowish-brown crystals precipitated. The filtrate was extracted with methylene chloride. On removal of the solvent and trichlorobenzene by evaporation in vacuo, there remained a further 60 g of crude product. The crude substance was recrystallised from cyclohexane using active charcoal. The yield was 180 g of orange-red crystals, m.p. 178°–180° C.

EXAMPLE 2

Production of 2,3-dichloro-4-methyl-7-methylcarbamoyloxy-1H-inden-1-one of the formula

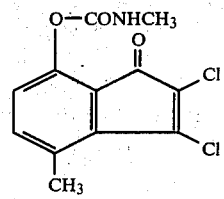

229 g of 2,3-dichloro-7-hydroxy-4-methyl-1H-inden-1-one was dissolved in a mixture of 1 liter of diethyl ether and 1 liter of tetrahydrofuran, and 1 ml of triethylamine was added. 69 g of methylisocyanate was added dropwise to this solution at 20°, the temperature rising to 28°. Crystallisation commenced after about 2 hours. After 20 hours, the crystal mass was filtered off under suction and washed with diethyl ether. The yield was 220 g of orange-yellow needles, m.p. 189°–190° (decomposition).

EXAMPLE 3

Production of 2,3-dichloro-7-hydroxy-4-methyl-6-nitro-1H-inden-1-one of the formula

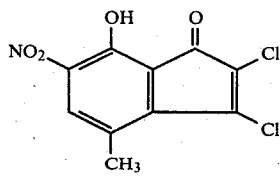

23 g of 2,3-dichloro-7-hydroxy-4-methyl-1H-inden-1-one was suspended in 250 ml of glacial acetic acid, and this mixture was warmed to 40° with stirring. There was then slowly added dropwise 10.5 g of 65% nitric acid (d=1.4), whereupon a clear deep-yellow solution was formed, and the reaction mixture was stirred at 40° for a further 3 hours. After standing for 15 hours, the mixture was stirred up with 500 ml of water; the yellow crystals were then filtered off with suction, and recrystallized whilst still moist from alcohol. There was obtained 16 g of yellow needles, m.p. 168°–170°.

EXAMPLE 4

(a) Production of 5-bromo-2-hydroxyphenyl-trichlorovinyl ketone (intermediate) of the formula

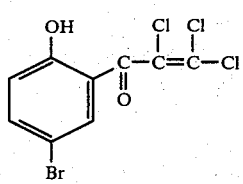

94 g of 4-bromanisole and 110 g of trichloroacrylic acid chloride were dissolved in 800 ml of dichloromethane, and 99 g of anhydrous aluminium chloride was added portionwise. The reaction mixture was then refluxed for 24 hours, with hydrogen chloride escaping. After cooling, there was slowly added dropwise, with continuous stirring, 0.5 N hydrochloric acid until two clear phases were formed. After concentration by evaporation, the dichloromethane phase yielded 130 g of a greenish oil, which was distilled under high vacuum. The main fraction boiled at 102°–105° and 0.02 mbar. The distillate solidified to give 101 g of yellow crystals, m.p. 61°–64°.

The following further starting materials of the formula IV were produced in an analogous manner:

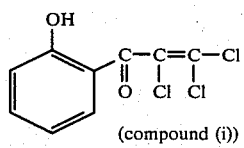

b.p. 95–100°/0,012 mbar (compound (i))

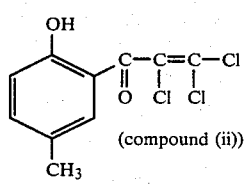

m.p. 55–58°

(compound (ii))

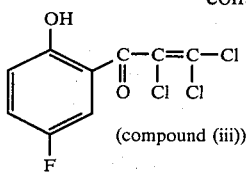

m.p. 59–62°

(compound (iii))

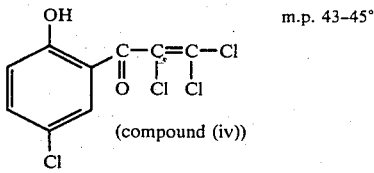

m.p. 43–45°

(compound (iv))

(b) Production of 4-bromo-2,3-dichloro-7-hydroxy-1H-inden-1-one of the formula

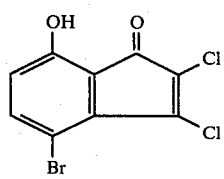

60 g of 5-bromo-2-hydroxy-phenyl-trichlorovinyl ketone was dissolved in 150 ml of 1,2,4-trichlorobenzene, and 33 g of aluminium chloride was added portionwise with stirring. The reaction mixture was firstly heated to 80°, and then slowly to 140°; and after 4 hours, the dark-brown mass was decomposed with ice-water and 0.5 N hydrochloric acid. After extraction with dichloromethane and removal of the of the solvent by distillation in vacuo, a dark semicrystalline substance was obtained. This was digested with 250 ml of ice-cold methanol and filtered under suction; and the brown crystalline product was recrystallised from cyclohexane/toluene and active charcoal. The yield was 20 g of light-yellow crystals, m.p. 170°–172°.

EXAMPLE 5

Production of 4-bromo-2,3-dichloro-7-methoxycarbonyloxy-1H-inden-1-one of the formula

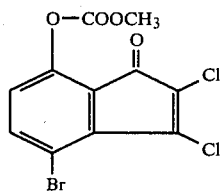

13 g of 4-bromo-2,3-dichloro-7-hydroxy-1H-inden-1-one was dissolved in 200 ml of tetrahydrofuran; 5 g of triethylamine was then added, and to the deep-red solution at 5°–10° there was added dropwise 4.5 g of chloroformic acid methyl ester. The reaction mixture was stirred at room temperature for a further 3 hours; the triethylammonium chloride was subsequently filtered off with suction and the filtrate was evaporated off in vacuo. The crystalline product was recrystallised from ethanol to yield 12 g of yellow crystals, m.p. 135°–137°.

The following compounds of the formula I can be produced in an analogous manner or by one of the methods described herein:

TABLE I ($R_1 = H$)

| Comp. No. | $R_2$ | $R_3$ | Physical constants |
|---|---|---|---|
| 1.1 | H | H | m.p. 147–148° |
| 1.2 | H | CH$_3$ | m.p. 178–180° |
| 1.3 | H | F | m.p. 171–173° |
| 1.4 | H | Cl | m.p. 170–171° |
| 1.5 | H | Br | m.p. 172–173° |
| 1.6 | 6-NO$_2$ | CH$_3$ | m.p. 168–170° |
| 1.7 | 6-Br | CH$_3$ | m.p. 133–135° |
| 1.8 | 6-NO$_2$ | Cl | m.p. 147–149° |
| 1.9 | 6-Cl | Cl | |
| 1.10 | 5-F | H | |
| 1.11 | 5-Cl | H | |

TABLE II

| Comp. No. | $R_2$ | $R_3$ | $R_1$ | Physical constants |
|---|---|---|---|---|
| 2.1 | H | CH$_3$ | —CONHCH$_3$ | m.p. 190° (decomp.) |
| 2.2 | H | CH$_3$ | —CONH—⟨phenyl⟩—Cl | m.p. 152–154° |
| 2.3 | H | CH$_3$ | —CONHC$_4$H$_9$(n) | m.p. 141–143° |
| 2.4 | H | CH$_3$ | —COOCH$_3$ | m.p. 136–138° |
| 2.5 | H | Cl | —CONHCH$_3$ | m.p. 180–182° |
| 2.6 | H | Cl | —COSC$_2$H$_5$ | m.p. 85–88° |
| 2.7 | H | Cl | —CO—CH═CH$_2$ | m.p. 153–155° |
| 2.8 | H | CH$_3$ | —CO—CCl═CCl$_2$ | m.p. 116–118° |
| 2.9 | H | F | —CONHCH$_3$ | m.p. 216–218° |
| 2.10 | H | Br | —COOCH$_3$ | m.p. 135–137° |
| 2.11 | H | Cl | —COCH$_3$ | m.p. 115–117° |
| 2.12 | H | F | —COCH$_2$Cl | m.p. 143–145° |
| 2.13 | 6-NO$_2$ | CH$_3$ | —CONH—CH$_3$ | m.p. 159–161 |
| 2.14 | H | CH$_3$ | —CONH—C$_2$H$_5$ | m.p. 186–188° |

Formulation Examples

Dust: The following substances are used to produce (a) a 5% dust and (b) a 2% dust:

(a)

5 parts of active substance,
95 parts of talcum;

(b)

2 parts of active substance,
1 part of highly dispersed silicic acid, and
97 parts of talcum.

The active substances are mixed and ground with the carriers, and in this form they can be applied by dusting.

Granulate: The following substances are used to produce a 5% granulate:

5 parts of active substance,
0.25 part of epichlorohydrin,
0.25 part of cetyl polyglycol ether,
3.50 parts of polyethylene glycol, and
91 parts of kaolin (particle size 0.3–0.8 mm).

The active substance is mixed with epichlorohydrin and dissolved in 6 parts of acetone, and the polyethylene glycol and cetyl polyglycol ether are then added. The solution obtained is sprayed onto kaolin, and the acetone is evaporated off in vacuo. A microgranulate of this type is advantageously used for combating soil fungi.

Wettable powder: The following constituents are used to produce (a) a 70% wettable powder, (b) a 40% wettable powder, (c) and (d) a 25% wettable powder, and (e) a 10% wettable powder:

(a)

70 parts of active substance,
5 parts of sodium dibutylnaphthylsulfonate,
3 parts of naphthalenesulfonic acid/phenolsulfonic acid/formaldehyde condensate (3:2:1),
10 parts of kaolin, and
12 parts of Champagne chalk;

(b)

40 parts of active substance,
5 parts of sodium lignin sulfonate,
1 part of sodium dibutylnaphthylsulfonate, and
54 parts of silicic acid;

(c)

25 parts of active substance,
4.5 parts of calcium lignin sulfonate,
1.9 parts of Champagne chalk/hydoxyethyl cellulose mixture (1:1),
1.5 parts of sodium dibutylnaphthyl sulfonate,
19.5 parts of silicic acid,
19.5 parts of Champagne chalk, and
28.1 parts of kaolin;

(d)

25 parts of active substance,
2.5 parts of isooctylphenoxy-polyoxyethyleneethanol,
1.7 parts of Champagne chalk/hydroxyethylcellulose mixture (1:1),
8.3 parts of sodium aluminium silicate,
16.5 parts of kieselgur, and
46 parts of kaolin; and (e)

10 parts of active substance,
3 parts of a mixture of the sodium salts of saturated fatty alcohol sulfates,
5 parts of naphthalenesulfonic acid/formaldehyde condensate, and
82 parts of kaolin.

The active substances are intimately mixed in suitable mixers with the additives, and the mixture is then ground in applicable mills and rollers. There are obtained wettable powders which have excellent wetting and suspension properties, which can be diluted with water to give suspensions of the desired concentration, and which in this form are particularly suitable for leaf application.

Emulsion concentrate: The following substances are used to produce a 25% emulsifiable concentrate:

25 parts of active substance,
2.5 parts of epoxidised vegetable oil,
10 parts of an alkylarylsulfonate/fatty alcohol polyglycol ether mixture,
5 parts of dimethylformamide, and
57.5 parts of xylene.

Emulsions of the concentration desired can be prepared from these concentrates by dilution with water, and they are particularly suitable for leaf application.

BIOLOGICAL EXAMPLES

EXAMPLE 6

Action Against *Puccinia graminis* on wheat (a) Residual Protective Action

Six days after being sown, wheat plants were sprayed with a spray liquor prepared from wettable powder of the active substance (0.06% of active substance). After 24 hours, the treated plants were infested with a uredospore suspension of the fungus. After an incubation time of 48 hours at about 20° C. with 95–100% relative humidity, the infested plants were kept in a greenhouse at about 22° C. An assessment of the development of rust pustules was made 12 days after infestation.

(b) Systemic Action

A spray liquor produced from wettable powder of the active substance (0.006% of active substance, relative to the volume of soil) was applied to the soil of wheat plants 5 days after sowing. After 48 hours, the treated plants were infested with a uredospore suspension of the fungus. After an incubation time of 48 hours at about 20° C. with 95–100% relative humidity, the infested plants were kept in a greenhouse at about 22° C. An assessment of the development of rust pustules was made 12 days after infestation.

EXAMPLE 7

Action Against *Cercospora arachidicola* on groundnut plants

Residual Protective Action

Groundnut plants 10–15 cm in height were sprayed with a spray liquor produced from wettable powder of the active substance (0.02% of active substance); and 48 hours later they were infested with a conidiospore suspension of the fungus. The infested plants were incubated for 72 hours at about 21° C. with high relative humidity, and were subsequently kept in a greenhouse until the typical leaf spots has appeared. The assessment of the fungicidal action was made 12 days after infestation, and was based on the number and size of the occurring spots.

EXAMPLE 8

Action Against *Botrytis cinerea* on broad beans

Broad bean plants about 10 cm in height were sprayed with a spray liquor produced from wettable powder of the active substance (0.02% of active substance); and after 24 hours, the treated plants were infested with a conidiospore suspension of the fungus. After incubation of the infested plants for 2–3 days with 95–100% relative humidity at 21° C., an assessment of the extent of fungus infection was made.

EXAMPLE 9

Action Against *Piricularia oryzae* on rice plants (a) Residual Protective Action After two-weeks' cultivation, rice plants were sprayed with a spray liquor produced from wettable powder of the active substance (0.02% of active substance). After 48 hours, the treated plants were infested with a conidiospore suspension of the fungus. The extent of fungus infection present was assessed after 5 days' incubation at 24° C. with 95–100% relative humidity.

(b) Systemic Action

A spray liquor produced from wettable powder of the active substance (0.006% of active substance, relative to the volume of soil) was applied to the surface of the soil of two-week-old rice plants. The pots were then filled with water to the extent that the lowest parts of the stalks of the rice plants were in water. After 48 hours, the treated plants were infested with a conidiospore suspension of the fungus. After incubation of the plants during 5 days at about 24° C. with 95–100% humidity, the degree of fungus infection was assessed.

EXAMPLE 10

Action Against *Tilletia caries*

Tilletia spores were suspended in a spray liquor containing 600 ppm of active substance for 15 minutes. The spore/active substance mixture was applied dropwise by pipette to the surface of finely sieved moist soil in Petri dishes. The soil dishes prepared in this way were kept at a temperature of 20° C. with high relative humidity. After about 10 days, spore germination was assessed under a microscope. The action of the test substances was assessed on the basis of the number and length of the germ tubes.

EXAMPLE 11

Action Against *Plasmopara viticola* on grape vines

Residual Protective Action

Young grape-vine seedlings in the 4–5-leaf stage were sprayed with a spray liquor produced from wettable powder of the active substance (0.06% of active substance). After 24 hours, the treated plants were infested with a sporangia suspension of the fungus. After an incubation time of 6 days at 20° C. with 95–100% relative humidity, an assessment of fungus infection was made.

EXAMPLE 12

Action Against *Venturia inaequalis* on apple trees

Residual Protective Action

Young apple seedlings having about 5 developed leaves were sprayed with a spray liquor produced from wettable powder of the active substance (0.06% of active substance). After 24 hours, the treated plants were infested with a conidiospore suspension of the fungus. The plants were incubated for 5 days with 90–100% relative humidity, and were then kept for a further 10 days in a greenhouse at 20°–24° C. The extent of scab infection was assessed 15 days after infestation.

The compounds according to the invention exhibited in general a good fungicidal action in the preceding tests. Compared with the infection present on untreated but infested control plants, the level of infection on the treated plants had been reduced to less than 20% by, among other compounds of the formula I, those compounds of the invention which are listed below:

against *Puccinia graminis:* Compounds Nos. 1.2, 1.3, 1.4, 1.5, 2.2, 2.5, 2.9, 2.10, 2.11, 2.12, (i), (iii) and (iv);

against *Cercospora arachidicola:* Compounds Nos. 2.3, 2.5, 2.6, 2.7, 2.9, 2.10, (i) and (iv);

against *Botrytis cinerea:* Compounds Nos. 1.3, 1.4, 1.5 and 2.5;

agaInst *Piricularia oryzae:* Compounds Nos. 1.3, 1.4, 2.1, 2.11, 2.14, 2.9 and (iv);

against *Tilletia caries:* Compound No. 2.5;

against *Plasmopara viticola:* Compounds Nos. 1.4 and 2.1; and against *Venturia inaequalis:* Compounds Nos. 1.4 and 2.1.

EXAMPLE 13

Action Against *Xanthomonas oryzae* on rice plants (a) Residual Protective Action Rice plants of the "Caloro" or "S6" variety were sprayed after 3 weeks' cultivation in a greenhouse with the test substance in the form of a spray liquor (0.06% of active substance). The sprayed-on coating was allowed to dry for one day, and the plants were then transferred to a climatic chamber at 24° C. with 75–85% relative humidity and infected. The infection was introduced by cutting off the leaf-tips with scissors which had previously been immersed in a suspension of Xanthomonas oryzae. After an incubation period of 10 days in the same chamber, the leaves which had been cut became withered, rolled up and became necrotic. The extent of these disease symptoms served as a basis for the assessment of the residual effectiveness of the test substance.

(b) Systemic Action

A suspension of the test substance (0.006% of active substance, relative to the volume of soil) was applied, after a cultivation time of 3 weeks, to the soil of rice plants of the "Caloro" or "S6" variety grown in flower pots. Three days after this treatment, the plants were transferred to a climatic chamber at 24° C. with 75–85% relative humidity and infected. The infection was imparted by the tips of the leaves being cut off with scissors which had previously been immersed in a suspension of *Xanthomonas oryzae.* After 10 days' incubation in the same chamber, the leaves which had been cut became withered, rolled up and became necrotic. The extent of these disease symptoms on the test plants served as a basis for the assessment of the systemic effectiveness of the test substance.

In the above tests 13 a and b, the compounds of the formulae I and IV exhibited a good action. The treated plants displayed no symptoms of wilt or of necrosis.

EXAMPLE 14

Action Against *Xanthomonas vesicatoria* on paprika plants (a) Residual Protective Action After 3-weeks' cultivation in a greenhouse, paprika plants of the "California Wonder" variety were sprayed with the test substance in the form of a spray liquor (0.06% of active substance). This sprayed-on coating was allowed to dry for one day; the plants were subsequently transferred to a climatic chamber at 26° C. with 95–100% relative humidity, and were infested by spraying of the underside of the leaves with a standardised suspension of *Xanthomonas vesicatoria.* After an incubation time of six days in the same chamber, there were formed on the leaves of the control plants round, lighter-coloured spots, which were initially watery and later necrotic. The extent of these spots on the test plants served as a basis for evaluating the residual action of the test substance.

(b) Systemic Action

A suspension of the test substance (0.006% of active substance, relative to the volume of soil) was applied, after 3-weeks' cultivation, to the soil of paprika plants of the "California Wonder" growing in flower pots. Three days after this treatment, the plants were placed into a climatic chamber at 26° C. with 95–100% relative humidity; the plants were then infested, by spraying of the underside of the leaves, with a standardised suspension of *Xanthomonas vesicatoria.* After an incubation time of six days in the same chamber, there were formed on the leaves of the control plants round, lighter-coloured spots, which were initially watery and later necrotic. The extent of these spots serves as a basis in assessing the systemic action of the test substance.

In the above tests 14 a and b, there was exhibited a good action by, inter alia, the compounds Nos. 1.2, 1.3, (iii) and (iv).

What is claimed is:

1. A 2,3-dichloro-7-carbamoyloxy-1H-inden-1-one derivative of the formula

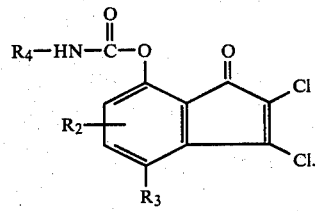

wherein $R_2$ and $R_3$ independently of one another are each hydrogen fluorine, chlorine, bromine, $C_1$–$C_4$-alkyl, trifluoromethyl or nitro, and $R_4$ is hydrogen, $C_1$–$C_6$-alkyl or $C_2$–$C_4$-alkenyl, each of which is unsubstituted or substituted by halogen, or $R_4$ is phenyl which is unsubstituted or is substituted by $C_1$–$C_4$-alkyl, $C_1$–$C_4$-alkoxy, halogen, trifluoromethyl, cyano or nitro, or it is a $C_3$–$C_6$-cycloalkyl group.

2. A compound according to claim 1 wherein $R_2$ is hydrogen, or in the 6-position it is nitro, fluorine, chlorine or bromine, or in the 5-position fluorine, chlorine or bromine; $R_3$ is hydrogen, fluorine, chlorine, bromine or $C_1$–$C_4$-alkyl; and $R_4$ is $C_1$–$C_4$-alkyl or $C_2$–$C_3$-alkenyl, each of which is unsubstituted or substituted by halogen.

3. A compound according to claim 2, wherein $R_2$ is hydrogen, or in the 6-position it is nitro or halogen.

4. A compound according to claim 2 or 3, wherein in the formula I $R_4$ is methyl or ethyl.

5. The compound 2,3-chloro-4-methyl-7-methylcarbamoyloxy-1H-inden-1-one.

6. A microbicidal composition containing as active ingredient an effective amount of a compound according to claim 1, together with suitable carriers.

7. A method for combatting microorganisms which comprises applying to said microorganisms or to the habitat thereof a pesticidally effective amount of a compound according to claim 1.

8. A method according to claim 7 wherein, in the compound, $R_2$ is hydrogen; nitro, fluorine, chlorine or bromine in the 6-position; or fluorine, chlorine or bromine in the 5-position, $R_3$ is hydrogen, fluorine, chlorine, bromine or $C_1$-$C_4$-alkyl, and $R_4$ is $C_1$-$C_4$-alkyl or $C_2$-$C_3$-alkenyl, each of which is unsubstituted or substituted by halogen.

9. A method according to claim 8 in which, in the compound, $R_2$ is hydrogen, or nitro or halogen in the 6-position.

10. A method according to claim 8 or 9 in which, in the compound, $R_4$ is methyl or ethyl.

11. The method according to claim 10 in which the compound is 2,3-dichloro-4-methyl-7-methylcarbamoyloxy-1H-inden-1-one.

12. A method according to claim 7 in which the microorganisms combatted are phytopathogenic fungi.

13. A method according to claim 7 in which the microorganisms combatted are phytopathogenic bacteria.

* * * * *